(12) United States Patent
Kondo et al.

(10) Patent No.: US 11,353,600 B2
(45) Date of Patent: Jun. 7, 2022

(54) RADIATION IMAGING APPARATUS

(71) Applicant: CANON KABUSHIKI KAISHA, Tokyo (JP)

(72) Inventors: Hiroto Kondo, Machida (JP); Masataka Suzuki, Yokohama (JP); Atsushi Takeuchi, Yokohama (JP); Riku Egawa, Kawasaki (JP); Hidetomo Suwa, Machida (JP); Shichihei Sakuragi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/823,111

(22) Filed: Mar. 18, 2020

(65) Prior Publication Data

US 2020/0309967 A1    Oct. 1, 2020

(30) Foreign Application Priority Data

Mar. 27, 2019   (JP) .............................. JP2019-060757

(51) Int. Cl.
 *A61B 6/00* (2006.01)
 *G01T 1/20* (2006.01)
 *G01N 23/04* (2018.01)

(52) U.S. Cl.
 CPC .......... *G01T 1/2018* (2013.01); *A61B 6/4233* (2013.01); *A61B 6/4283* (2013.01); *A61B 6/4405* (2013.01); *G01N 23/04* (2013.01)

(58) Field of Classification Search
 CPC .... G01T 1/2018; G01N 23/04; A61B 6/4233; A61B 6/4283; A61B 6/4405; A61B 6/00; G03B 42/04
 See application file for complete search history.

(56) References Cited

U.S. PATENT DOCUMENTS

| | | | | |
|---|---|---|---|---|
| 2010/0254517 A1* | 10/2010 | Watanabe | .............. | G03B 42/04 378/154 |
| 2012/0163555 A1* | 6/2012 | Watanabe | ................ | A61B 6/06 378/154 |
| 2012/0280601 A1* | 11/2012 | Watanabe | .............. | G03B 42/04 312/223.1 |
| 2013/0051531 A1* | 2/2013 | Kobayashi | ........... | A61B 6/4283 378/98 |
| 2015/0342553 A1* | 12/2015 | Sato | .......................... | G01T 7/00 250/336.1 |
| 2016/0135766 A1* | 5/2016 | Tateishi | ............... | A61B 6/4266 250/370.09 |

(Continued)

FOREIGN PATENT DOCUMENTS

| | | |
|---|---|---|
| JP | 2015-051206 A | 3/2015 |
| JP | 5979839 B2 | 8/2016 |

(Continued)

*Primary Examiner* — Mark R Gaworecki

(74) *Attorney, Agent, or Firm* — Canon U.S.A., Inc. I.P. Division

(57) ABSTRACT

In a radiation imaging apparatus, a first recessed portion is formed in at least one side surface among a plurality of side surfaces forming a frame body of a casing. Moreover, a second recessed portion is formed in a peripheral region of a back surface of a back-surface housing, which is a region opposite to the first recessed portion with respect to a boundary between the back surface and the at least one side surface of the casing including the first recessed portion.

14 Claims, 7 Drawing Sheets

(56) References Cited

U.S. PATENT DOCUMENTS

| | | | | |
|---|---|---|---|---|
| 2016/0367194 | A1* | 12/2016 | Murphy | A61B 5/6898 |
| 2017/0066929 | A1* | 3/2017 | Nariyuki | C09D 7/40 |
| 2017/0090044 | A1* | 3/2017 | Suzuki | A61B 6/4283 |
| 2018/0140750 | A1* | 5/2018 | Shibata | A61B 90/70 |
| 2019/0011574 | A1* | 1/2019 | Suwa | A61B 6/4488 |
| 2019/0110376 | A1* | 4/2019 | Tagawa | G01T 1/2006 |
| 2019/0293812 | A1* | 9/2019 | Suzuki | G01T 7/00 |

FOREIGN PATENT DOCUMENTS

| | | | |
|---|---|---|---|
| JP | 6080900 | B2 | 2/2017 |
| JP | 2017-086768 | A | 5/2017 |
| JP | 2017086768 | A * | 5/2017 |

\* cited by examiner

RADIATION IMAGING APPARATUS

BACKGROUND OF THE DISCLOSURE

Field of the Disclosure

The present disclosure relates to a portable radiation imaging apparatus to be used in, for example, a medical field.

Description of the Related Art

In the medical field, there has been widely used a radiation imaging apparatus (adopting DR: Digital Radiography) configured to obtain a radiation image through use of a semiconductor sensor. Such an imaging apparatus is required to have portability and high operability, and hence is now being reduced in size, thickness, and weight. Thus, in recent years, a large number of wireless-type imaging apparatus have been widely used.

Meanwhile, as requirements for portability, not only lightness but also stable and comfortable holding of the imaging apparatus is important. In Japanese Patent No. 6080900, there is disclosed an imaging apparatus including a housing with a recessed portion. In Japanese Patent No. 5979839, there is disclosed an X-ray imaging apparatus in which a dent is defined in a joining portion between two housing components forming a housing.

It is important to consider not only comfortable holding of a portable radiation imaging apparatus but also easy lifting of the portable radiation imaging apparatus. Among wireless-type imaging apparatus, a model including a replaceable battery has such a problem that it is difficult to lift the imaging apparatus in a case in which an incident surface that a radiation enters (or a back surface opposed to the incident surface) is laid on a flat surface such as a desk or a table with the incident surface side (or the back surface) down when the battery is mounted or removed.

SUMMARY OF THE DISCLOSURE

According to one embodiment of the present disclosure, there is provided a radiation imaging apparatus, including a radiation detector arranged to convert a radiation transmitted through an object into an electrical signal; and a casing arranged to surround the radiation detector, the casing having a rectangular parallelepiped shape, and including an incident surface that the radiation enters, a back surface opposed to the incident surface, and a plurality of side surfaces located between the incident surface and the back surface, wherein a first recessed portion is formed in at least one side surface among the plurality of side surfaces, and a second recessed portion is formed in a peripheral region of the back surface, which is a region opposite to the first recessed portion with respect to a boundary between the back surface and the at least one side surface including the first recessed portion.

Further features and aspects of the present disclosure will become apparent from the following description of example embodiments with reference to the attached drawings.

DESCRIPTION OF THE EMBODIMENTS

According to an embodiment of the present disclosure, an operator can smoothly perform operation of lifting the imaging apparatus under a state in which the imaging apparatus is placed on a flat surface.

Example embodiments of the present disclosure will now be described in detail in accordance with the accompanying drawings.

First Example Embodiment

Figure 1A:
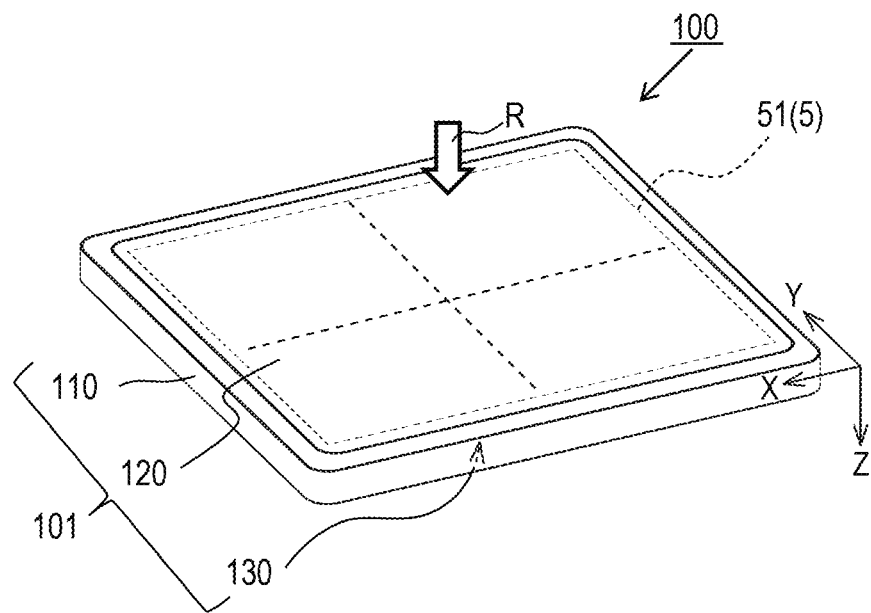
FIG. 1A is a perspective view for illustrating an example radiation imaging apparatus according to the present disclosure.
Figure 1B:
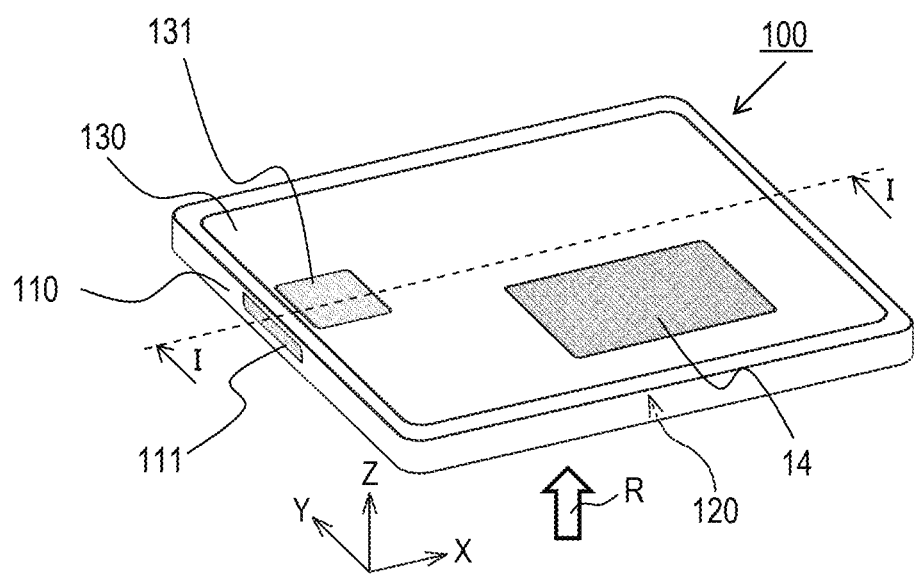
FIG. 1B is a perspective view for illustrating the radiation imaging apparatus according to the present disclosure.

A first example embodiment is herein described below. FIG. 1A and FIG. 1B are views for illustrating an external appearance of a radiation imaging apparatus (hereinafter referred to as "imaging apparatus") 100 according to the present embodiment. An XYZ coordinate system illustrated in FIG. 1A and FIG. 1B corresponds to an XYZ coordinate system illustrated in the other drawings.

FIG. 1A is a view for illustrating the imaging apparatus 100 seen from a side of a radiation incident surface (hereinafter referred to as "incident surface") that a radiation R enters. The imaging apparatus 100 includes a casing 101 arranged to surround a radiation detector (hereinafter referred to as "detector") 5. The casing 101 includes a frame body 110, a radiation transmission plate (hereinafter referred to as "transmission plate") 120, and a back-surface housing 130. The frame body 110 forms a plurality of side surfaces. The transmission plate 120 includes the incident surface, and is joined to the frame body 110. The back-surface housing 130 includes a back surface opposed to the incident surface, and is joined to the frame body 110. An effective pixel region 51 of the detector 5 is illustrated by the dotted rectangle. In the illustrated XYZ coordinate system, an incident direction of the radiation R is defined as a Z-axis, and two mutually orthogonal axes, which are orthogonal to the Z-axis and define the incident surface of the transmission plate 120, are defined as an X-axis and a Y-axis.

FIG. 1B is a view for illustrating the imaging apparatus 100 seen from the back surface side. Radio wave transmission windows 111 and 131 configured to enable wireless communication are formed in a predetermined position of one side surface of the frame body 110 and a predetermined position of the back-surface housing 130, respectively. A power source cover 14 is arranged so as to maintain flatness of a surface of the back-surface housing 130.

Figure 2:
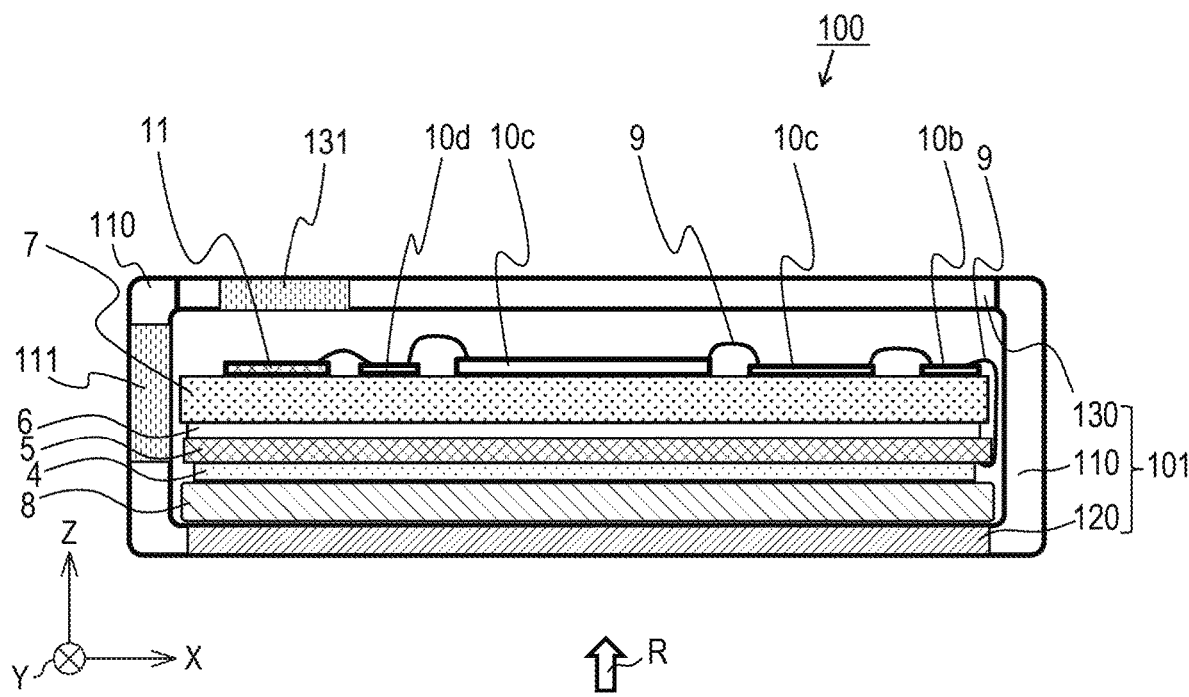
FIG. 2 is a sectional view for illustrating the radiation imaging apparatus taken along the line I-I of FIG. 1B.

FIG. 2 is a view for illustrating a schematic configuration of the imaging apparatus 100 in a cross section taken along the line I-I of FIG. 1B. The same components as the components illustrated in FIG. 1A and FIG. 1B are denoted by the same reference symbols (the same holds true for the other drawings).

Inside the casing 101, a scintillator layer 4 is laminated, and the detector (that may also be referred to as "sensor") 5 is provided. The scintillator layer 4 converts the radiation R transmitted through an object (object to be examined) into light. The detector 5 is arranged to convert the light emitted by the scintillator layer 4 into an electrical signal (image signal). The detector 5 is mounted to a sensor holding plate 7 through intermediation of a radiation shielding member 6. As a material for the scintillator layer 4, GOS ($Gd_2O_2S$) or CsI is often used. The detector 5 is formed of a glass substrate. Accordingly, the detector 5 breaks when receiving an intense shock or a load or undergoing displacement. Thus, on the incident surface side of the detector 5, a shock absorbing member 8 arranged to absorb the shock is arranged. As the shock absorbing member 8, materials having high radiation transmittance are selected in order to guide the radiation R transmitted through the object to the scintillator layer 4 while preventing attenuation as much as possible. The radiation shielding member 6 has a function of protecting, for example, electric substrates 10b and 10c from the radiation R transmitted through the object and the detector 5. In addition, the radiation shielding member 6 has a function of preventing the radiation R transmitted through the imaging apparatus 100 and scattered by, for example, a wall behind the imaging apparatus 100 from rebounding and entering the scintillator layer 4 and the detector 5 again. Thus, as the radiation shielding member 6, materials such as Mo, W, Pb, Al, Cu, SUS, and Barium sulfate are adopted.

On a surface of the sensor holding plate 7 on the back-surface housing 130 side, an electric substrate 10a (illustrated in FIG. 3), the electric substrates 10b and 10c, a communication module substrate 10d, and an antenna 11 for wireless communication are placed. The electric substrates 10a and 10b are configured to read the electrical signal converted by the detector 5 through wiring (that may also be referred to as "flexible printed circuit") 9. The electric substrate 10c is configured to generate radiation image data based on the read electrical signal. The radiation image data generated by the electric substrate 10c is sent to a display system (not shown) through the communication module substrate 10d and the antenna 11, and is displayed as a radiation image. Here, description is made of an example of performing wireless communication connection, but wired communication connection may also be performed. Further, when wireless communication connection is performed, the 2.4 GHz band or the 5 GHz band can be mainly used. Through such communication methods, the imaged radiation image data is transferred to, for example, a PC or a tablet computer to be checked by an operator.

In a case in which wireless communication connection is performed, when the casing 101 is made of a metal-based material, radio waves are interrupted. Thus, the radio wave transmission windows 111 and 131 are arranged in the casing 101. The antenna 11 is arranged at a position close to at least one of the radio wave transmission windows 111 and 131 in consideration of wireless radiation characteristics. Further, the radio wave transmission windows 111 and 131 may be integrated so as to extend astride adjacent side surfaces of the casing 101.

Figure 3:
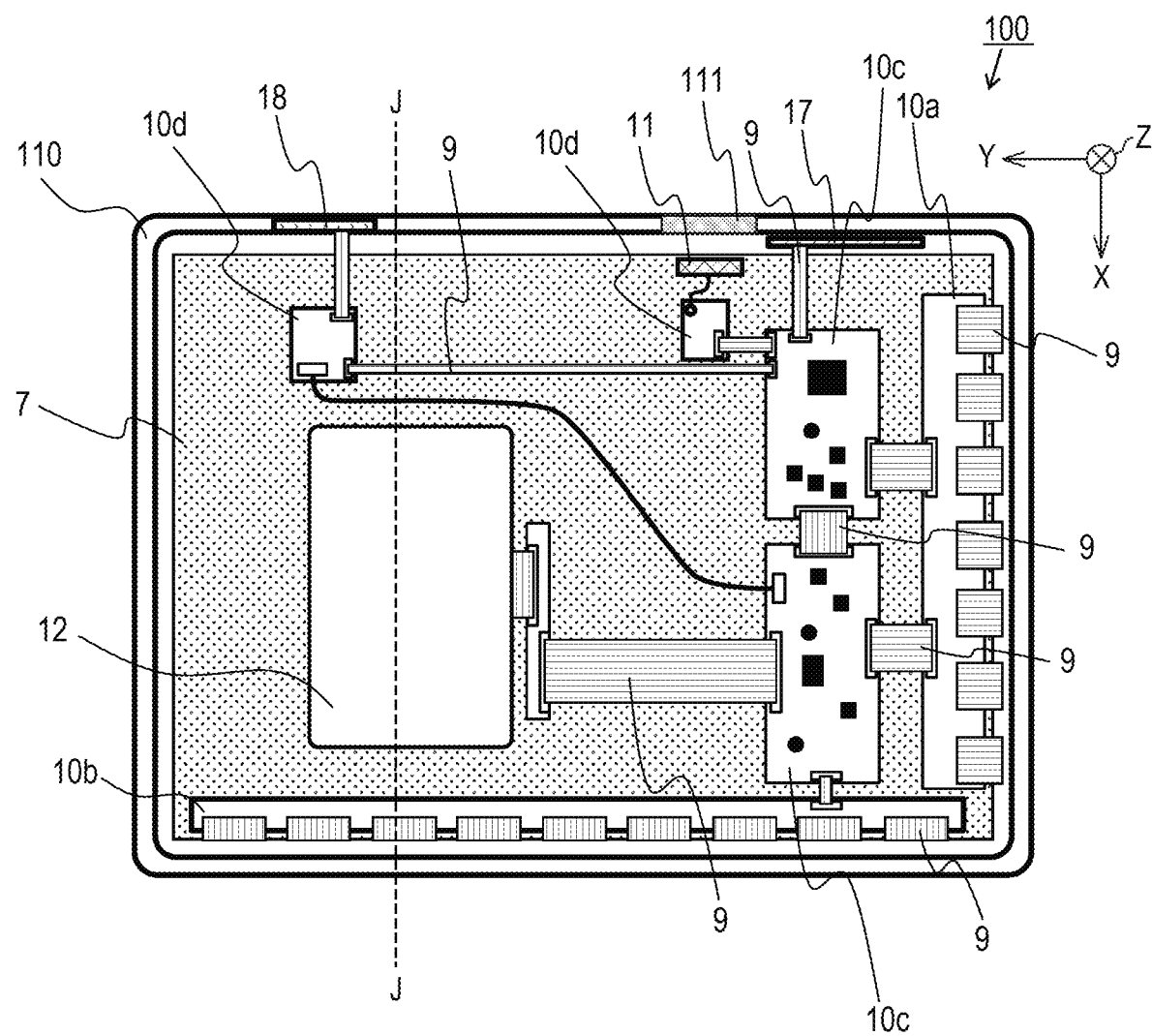
FIG. 3 is a schematic view for illustrating the internal structure of the radiation imaging apparatus according to the present disclosure seen from a back surface side thereof.

FIG. 3 is a schematic view for illustrating the internal structure of the imaging apparatus 100 seen from the back surface side thereof under a state in which the back-surface housing 130 is removed from the imaging apparatus 100 illustrated in FIG. 1B.

The imaging apparatus 100 is of a wireless type, and hence includes a power source 12 mounted therein and configured to drive the apparatus. The power source 12 is rechargeable, and hence a secondary battery such as a lithium-ion battery or a lithium-ion capacitor is adopted. The power source 12 may have the arrangement structure enabling an operator to make direct access to the power source 12 without removing the back-surface housing 130, and easily mount and remove the power source 12. An interface 17, for example, a power switch, and an external interface 18 for communication with an external unit or for power supply are arranged on the frame body 110.

Figure 4:
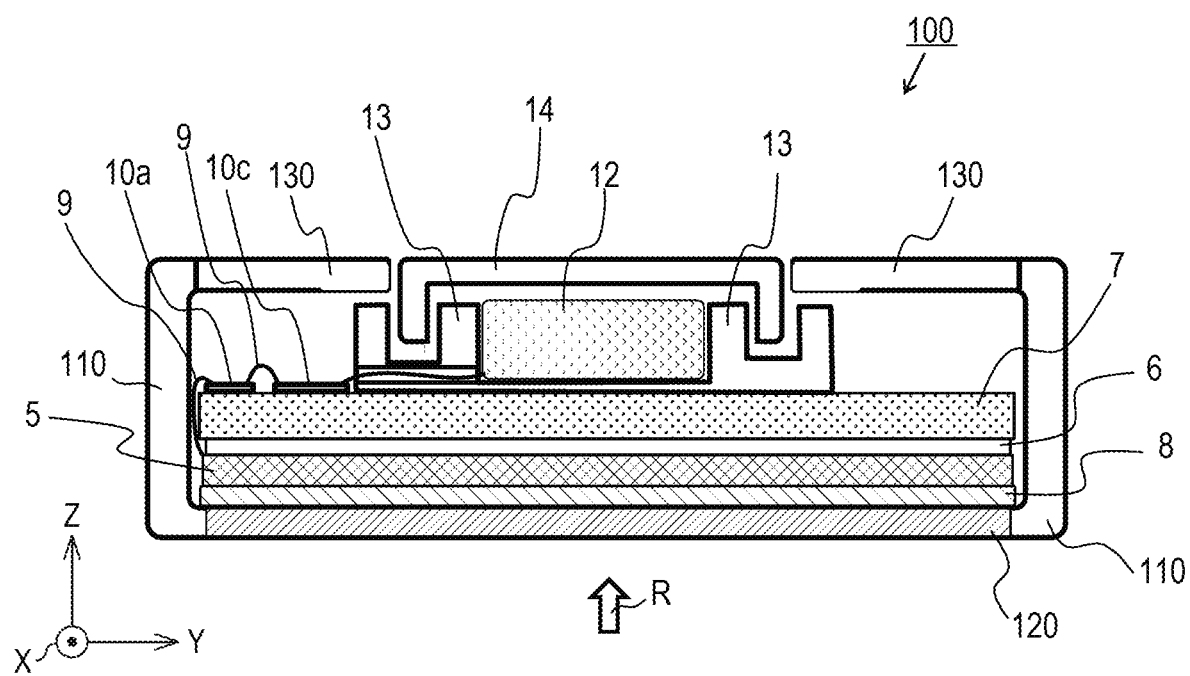
FIG. 4 is a sectional view for illustrating the radiation imaging apparatus taken along the line J-J of FIG. 3.

FIG. 4 is a view for illustrating an example of the mounting structure for the power source 12 illustrated in FIG. 3.

The power source 12 is fitted in a power source holder 13, and the power source cover 14 is mounted to the power source holder 13. In this manner, the power source 12 is held.

Figure 5A:
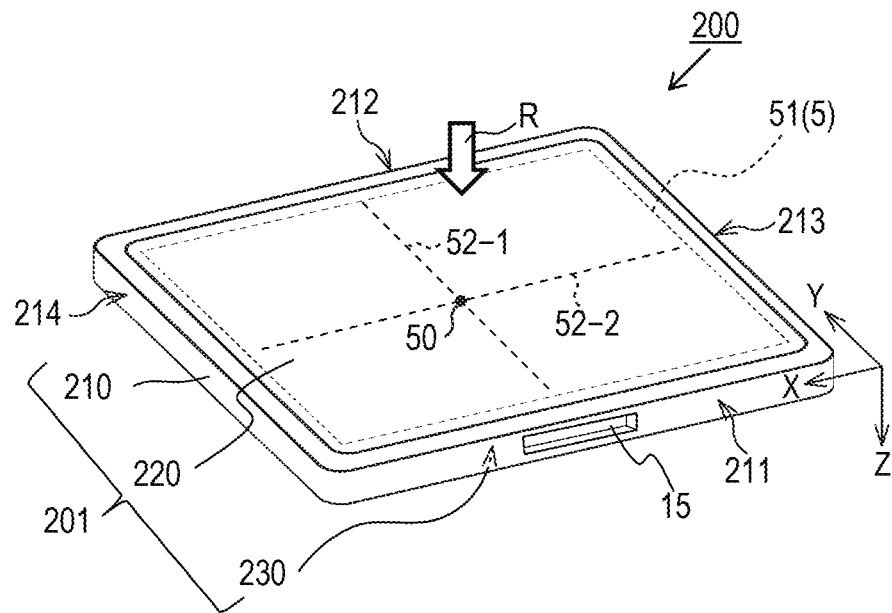
FIG. 5A is a perspective view for illustrating a radiation imaging apparatus according to a first example embodiment.
Figure 5B:
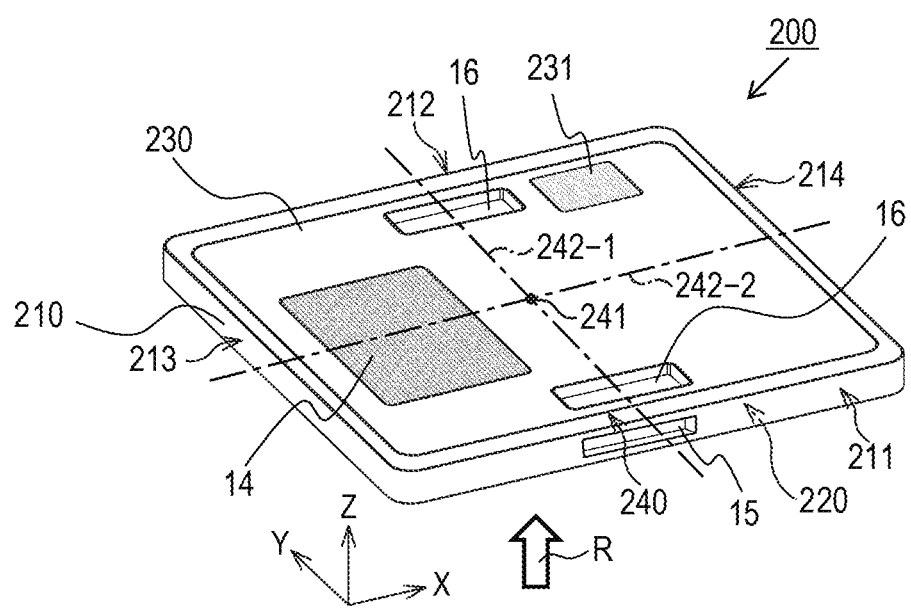
FIG. 5B is a perspective view for illustrating the radiation imaging apparatus according to the first example embodiment.

Next, another imaging apparatus according to the first embodiment is described. FIG. 5A and FIG. 5B are views for illustrating an external appearance of another imaging apparatus 200.

FIG. 5A is a view for illustrating the imaging apparatus 200 seen from the incident surface side. The imaging apparatus 200 includes a casing 201 surrounding the detector 5 arranged to convert the radiation R transmitted through the object into an electrical signal. The effective pixel region 51 of the detector 5 surrounded by the casing 201 is illustrated by the dotted rectangle. The casing 201 has a rectangular parallelepiped shape, and includes a frame body 210, a transmission plate 220, and a back-surface housing 230. The frame body 210 forms a plurality of side surfaces 211 to 214. The transmission plate 220 includes the incident surface that the radiation R enters, and is joined to the frame body 210. The back-surface housing 230 includes the back surface opposed to the incident surface, and is joined to the frame body 210.

It is required that the casing 201 of the imaging apparatus 200 be made of a material having a small weight and high strength. Thus, for example, CFRP, an aluminum alloy, or a magnesium alloy can be adopted. It is required that a material having a satisfactory transmittance to the radiation R entering the transmission plate 220 be selected for the transmission plate 220. When a metal material such as an aluminum alloy or a magnesium alloy is adopted as a material for the casing 201, it is preferred to adopt, for the transmission plate 220, a material, for example, CFRP, which has high rigidity and a high radiation transmittance.

A first recessed portion 15 is formed in one side surface 211 among the plurality of side surfaces 211 to 214 forming the frame body 210. In plan view seen from the incident direction of the radiation R, the first recessed portion 15 is located in a region containing positions on a line (line 52-1) which passes a center position 50 in the effective pixel region 51 of the detector 5 and extends along the Y-axis of the X-axis and the Y-axis, which are two axes orthogonal to each other and defining the incident surface of the transmission plate 220.

FIG. 5B is a view for illustrating the imaging apparatus 200 seen from a back surface side thereof. Radio wave transmission windows 231 (a window on a side surface side is not shown) corresponding to the radio wave transmission windows 111 and 131 of FIG. 1B are formed in a predetermined position of the back-surface housing 230 and a predetermined position of one side surface of the frame body 210, respectively.

Second recessed portions 16 are formed in the back-surface housing 230 in a peripheral region of the back surface, which is a region opposite to the first recessed portion 15 with respect to a boundary 240 between the back surface and the side surface 211 including the first recessed portion 15. In plan view seen from the incident direction of the radiation R, the second recessed portions 16 and the first recessed portion 15 are formed in a region containing positions on a line (line 242-1) which passes a gravity center position 241 of the imaging apparatus 200 and extends along the Y-axis of the X-axis and the Y-axis, which are two axes orthogonal to each other and defining the incident surface of the transmission plate 220. Here, in FIG. 5B, the gravity center position 241 of the imaging apparatus 200 is at substantially the same position as the center position 50 in the effective pixel region 51 of the detector 5 illustrated in FIG. 5A in an XY plane, but may be at a different position.

The first recessed portion 15 is formed so as to allow an operator to easily hold and lift the imaging apparatus 200 with his/her fingers under a state in which the imaging apparatus 200 is laid on a flat surface (state in which the transmission plate 220 or the back-surface housing 230 is laid on a flat surface). Further, the second recessed portions 16 are each structured to function as a gripped portion (finger receiving portion) at the time of carrying of the imaging apparatus 200. When a depth large enough to receive fingers is ensured, stable portability can be ensured.

In the imaging apparatus 200, in consideration of holding the first recessed portion 15 and the second recessed portion 16 with fingers, the first recessed portion 15 and the second recessed portion 16 are formed at positions adjacent to each other with respect to the boundary 240 between the side surface 211 of the frame body 210 and the back-surface housing 230. With this arrangement, even under a state in which the back-surface housing 230 is laid on a flat surface, an operator lifts at least one side of the imaging apparatus 200 through use of the first recessed portion 15, and reaches the second recessed portion 16 formed in the back surface immediately after spreading out his/her hand put on the first recessed portion 15. In this manner, an operator can grip the imaging apparatus 200. When even one of the second recessed portions 16 can be held with fingers, the imaging apparatus 200 can be stably lifted and carried, thereby being capable of smoothly performing operation of lifting and then carrying the imaging apparatus 200 placed on a flat surface.

Moreover, in consideration of stable carrying of the imaging apparatus 200, the second recessed portions 16 and the first recessed portion 15 can be formed in a region containing positions on the line 242-1.

Further, FIG. 5A and FIG. 5B are illustrations of an example in which the first recessed portion 15 is formed in the side surface 211 that is part of the plurality of side surfaces 211 to 214 forming the frame body 210. However, another first recessed portion 15 may be further formed in the side surface 212 so as to be matched with the second recessed portion 16.

Moreover, the first recessed portion 15 may be formed in every one of the plurality of side surfaces 211 to 214 forming the frame body 210. In this case, the first recessed portions 15 are formed in a region containing positions on the line 52-1 and positions on a line 52-2 illustrated in FIG. 5A or a region containing positions on the line 242-1 and positions on a line 242-2 illustrated in FIG. 5B.

In this case, four second recessed portions 16 may be formed in a peripheral region of the back-surface housing 230 so as to be matched with the first recessed portions 15, respectively. In this case, the second recessed portions 16 can be formed in the region containing positions on the line 242-1 and positions on the line 242-2 so that the second recessed portions 16 in each pair are opposed to each other.

Further, in consideration of holding and lifting the imaging apparatus with tips of fingers, the first recessed portion 15 can be a recessed portion having a depth equal to or larger than 1 mm. In this case, when holding the imaging apparatus with fingers, an operator feels less pain, and also can smoothly perform lifting operation. However, when it is inevitable to reduce the depth of the first recessed portion 15, the first recessed portion 15 may be improved through a change in edge shape or surface texture of the recessed portion.

Second Example Embodiment

Next, a second example embodiment is herein described below. In the following, description of matters common to the first embodiment is omitted, and different matters are described.

Figure 6:
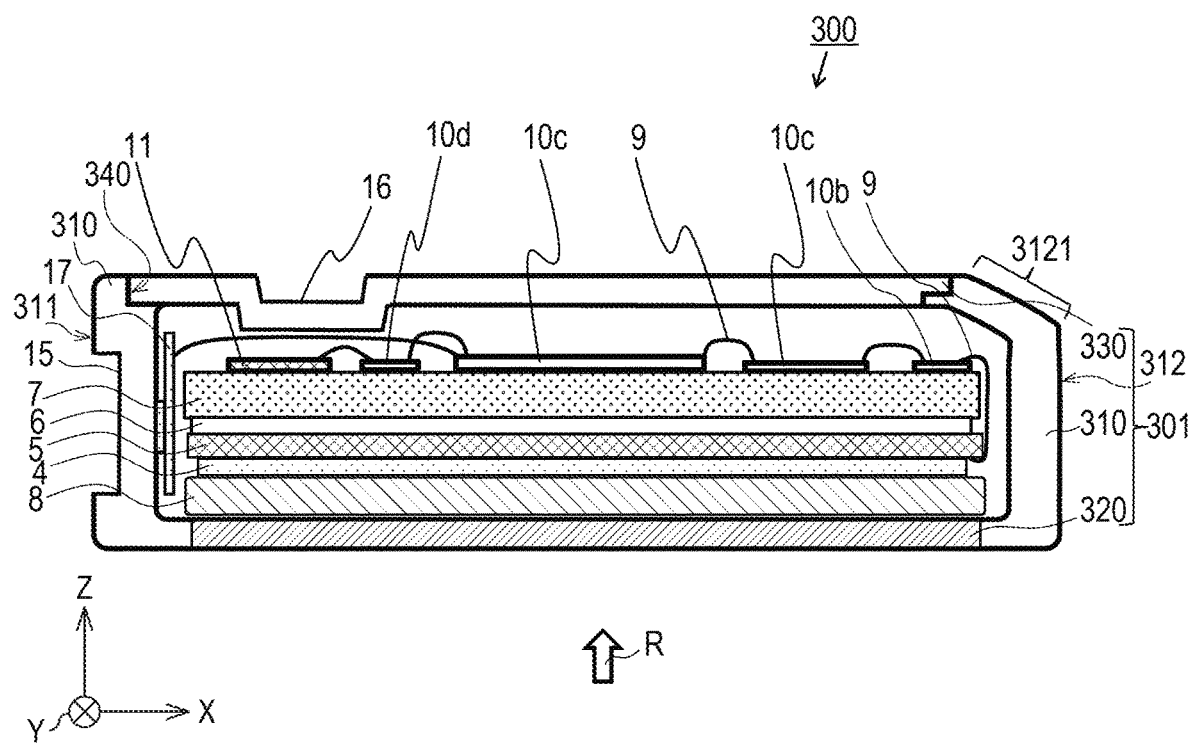
FIG. 6 is a sectional view for illustrating a radiation imaging apparatus according to a second example embodiment.

FIG. 6 is a view for illustrating a schematic configuration of an imaging apparatus 300 according to the second embodiment. The imaging apparatus 300 includes a casing 301 surrounding the detector 5 arranged to convert the radiation R transmitted through the object into an electrical signal. The casing 301 has a rectangular parallelepiped shape, and includes a frame body 310, a transmission plate 320, and a back-surface housing 330. The frame body 310 forms a plurality of side surfaces. The transmission plate 320 includes the incident surface that the radiation R enters, and is joined to the frame body 310. The back-surface housing 330 forms the back surface opposed to the incident surface, and is joined to the frame body 310.

Similarly to the first embodiment, inside the casing 301, the scintillator layer 4, the detector 5, the radiation shielding member 6, the sensor holding plate 7, the shock absorbing member 8, the wiring 9, the electric substrate 10a (not shown), the electric substrates 10b and 10c, the communication module substrate 10d, the antenna 11 for wireless communication, and the interface 17, for example, a power switch, are provided.

The first recessed portion 15 is formed in a side surface 311 that is part of the plurality of side surfaces forming the frame body 310. On a side surface 312 opposed to the side surface 311, an inclined region 3121 is formed to be inclined to the back-surface housing 330 side. In the first embodiment, description is made of the operation of holding and lifting the imaging apparatus with fingers put on the first recessed portion 15 formed in one position when the back-surface housing 330 is laid on a flat surface. However, when this operation is performed in the second embodiment, there is performed turning operation of turning the imaging apparatus about an edge of a portion corresponding to the inclined region 3121. In a case in which the imaging apparatus 300 has a large weight, when the turning operation is performed, owing to formation of the inclined region 3121 on the side surface 312 opposed to the first recessed portion 15, the entire imaging apparatus 300 is easily inclined. Thus, operation of lifting and then carrying the imaging apparatus 300 can be more smoothly performed.

In order to form the inclined region 3121 on the frame body 310, a clearance between the built-in detector 5 and the inclined region 3121 is important. The wiring 9 connected to the electric substrate 10a for a reading signal and to the electric substrate 10b for a drive signal are mounted on at least two sides of the detector 5 having a rectangular shape. On a side of the detector 5 on which the wiring 9 is not mounted, there are arranged a display system configured to display a state of the imaging apparatus 300, the interface 17, for example, a power switch, and the external interface 18 for communication with an external unit or for power supply. Thus, the side of the detector 5, on which a flexible board is mounted, affords a larger space in a thickness direction of the imaging apparatus 300 as the internal structure of the imaging apparatus 300, and it is preferred that the inclined region 3121 be formed on the side of the detector 5 on which a flexible board is mounted. Further, an operator often operates the imaging apparatus while raising the interface part. Thus, operability is better when the inclined region 3121 is formed on the side on which the wiring 9 connected to the detector 5 is mounted. That is, it is desired that the side surface 312 opposed to the side surface 311 including the first recessed portion 15 be a side surface arranged to sandwich the wiring 9 between the detector 5 and the side surface.

Further, similarly to the first embodiment, the second recessed portion 16 is formed in the back-surface housing 330 of the casing 301 in a region opposite to the first recessed portion 15 with respect to a boundary 340 between the back surface and the side surface 311 including the first recessed portion 15.

Third Example Embodiment

Next, a third example embodiment is described. In the following, description of matters common to the first and second embodiments is omitted, and different matters are described.

In the first embodiment, the lines 51(5), 52-1, and 52-2 are displayed on a surface of the transmission plate 220. Thus, an operator can visually recognize the effective pixel region 51. A wireless-type imaging apparatus is frequently used not only in a general radiation imaging room but also during ward round and at the site of emergency treatment. Under such circumstances, in many cases, the imaging apparatus is slid beneath the object, and alignment with a radiation source (not shown) is performed. Under a state in which the imaging apparatus is slid beneath the object, the center position 50 of the effective pixel region 51 cannot be visually recognized. Thus, when the center position 50 can be recognized at a touch of an outer shape of the imaging apparatus with fingers, the alignment is easily performed. In the third embodiment, an imaging apparatus given in consideration of this point is provided.

Figure 7:
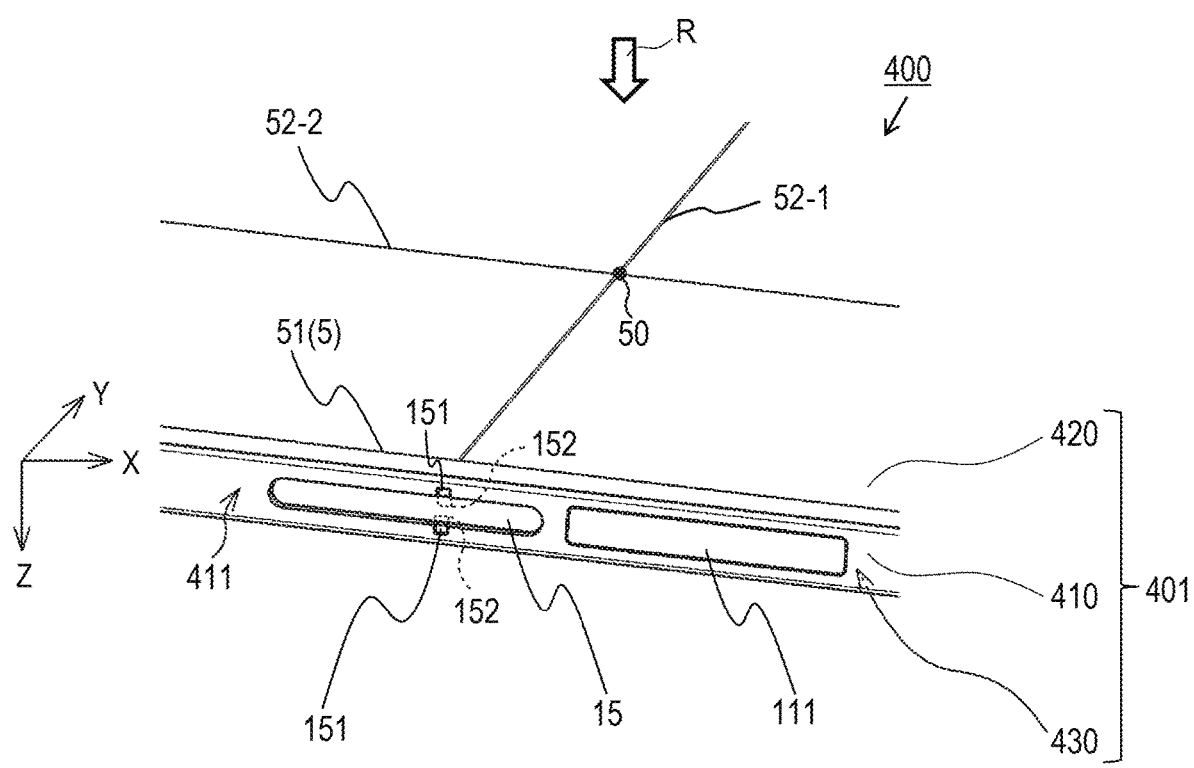
FIG. 7 is a schematic view for illustrating a part of a side surface portion of a radiation imaging apparatus according to a third example embodiment.

FIG. 7 is a view for illustrating an imaging apparatus 400 according to the third embodiment seen from a side of the incident surface that the radiation R enters. The imaging apparatus 400 according to the third embodiment includes, similarly to the imaging apparatus 200 according to the first embodiment, the above-mentioned components illustrated in FIG. 2 to FIG. 4. A casing 401 includes a frame body 410, a transmission plate 420, and a back-surface housing 430. The frame body 410 forms a plurality of side surfaces (only a side surface 411 is illustrated in FIG. 7). The transmission plate 420 includes the incident surface, and is joined to the frame body 410. The back-surface housing 430 includes a back surface opposed to the incident surface, and is joined to the frame body 410.

The first recessed portion 15 and the radio wave transmission window 111 are formed in the side surface 411 of the frame body 410. Similarly to the first embodiment, the first recessed portion 15 is formed in a region containing positions on the line 52-1.

Inside the first recessed portion 15, recessed structural portions 151 are formed to extend to an outer side of the first recessed portion 15. Each of the recessed structural portions 151 has a recessed shape, and is arranged to show the center position 50 in the effective pixel region 51 of the detector 5. The recessed structural portions 151 are formed at positions on the detector line 52-1. When an operator inserts his/her fingers in the first recessed portion 15 and puts his/her fingers on the recessed structural portions 151, the operator can recognize the center position 50 in a direction of the X-axis in the effective pixel region 51 of the detector 5.

Further, as indicated by the dotted lines in FIG. 7, inside the first recessed portion 15, protruding structural portions 152 may be formed to extend to an inner side of the first recessed portion 15. Each of the protruding structural portions 152 has a protruding shape, and is arranged to show the center position 50 in the effective pixel region 51 of the detector 5.

In the third embodiment, description is made of the example in which the first recessed portion 15 is formed in the region containing positions on the detector line 52-1 and the recessed structural portions 151 or the protruding structural portions 152 are formed inside the first recessed portion 15. However, the first recessed portion 15 may be formed in a region containing positions on the detector line 52-2, and the recessed structural portions 151 or the protruding structural portions 152 may be formed inside the first recessed portion 15. In this case, when an operator inserts his/her fingers in the first recessed portion 15 and puts his/her fingers on the recessed structural portions 151 or the protruding structural portions 152, the operator can recognize the center position 50 in a direction of the Y-axis in the effective pixel region 51 of the detector 5. Further, the recessed structural portions 151 or the protruding structural portions 152 are formed inside the first recessed portion 15, and hence the center position 50 in the effective pixel region 51 of the detector 5 can be recognized by an operator without increasing a size of the imaging apparatus 400.

While the present disclosure has been described with reference to example embodiments, it is to be understood that the disclosure is not limited to the disclosed example embodiments. The scope of the following claims is to be accorded the broadest interpretation so as to encompass all such modifications and equivalent structures and functions.

This application claims the benefit of Japanese Patent Application No. 2019-060757, filed Mar. 27, 2019, which is hereby incorporated by reference herein in its entirety.

What is claimed is:
1. A radiation imaging apparatus comprising:
a radiation detector arranged to convert a radiation transmitted through an object into an electrical signal; and
a casing arranged to surround the radiation detector, the casing having a rectangular parallelepiped shape, and including an incident surface that the radiation enters, a back surface opposed to the incident surface, and a plurality of side surfaces located between the incident surface and the back surface,
wherein an inclined region is formed to be inclined to the back surface side on a first side surface among the plurality of side surfaces, and is not formed on a second side surface opposite to the first side surface, and
wherein a first recessed portion is formed in the exterior of the second side surface, and is not formed in the exterior of the first side surface, and a second recessed portion is formed in a peripheral region of the back surface, which is a region opposite to the first recessed portion with respect to a boundary between the back surface and the second side surface.

2. The radiation imaging apparatus according to claim 1, wherein the casing includes:
a frame body forming the plurality of side surfaces;
a transmission plate including the incident surface, and being joined to the frame body; and
a back-surface housing including the back surface, and being joined to the frame body.

3. The radiation imaging apparatus according to claim 2, wherein the first recessed portion and the second recessed portion are arranged at positions adjacent to each other with respect to a boundary between a side surface of the frame body and the back-surface housing.

4. The radiation imaging apparatus according to claim 1, wherein on the opposed side surface, wiring connected to the radiation detector is arranged.

5. The radiation imaging apparatus according to claim 1, wherein the first recessed portion is formed in every one of the plurality of side surfaces.

6. The radiation imaging apparatus according to claim 1, wherein in plan view seen from an incident direction of the radiation, the first recessed portion is formed in a region containing positions on a line which passes a center position in an effective pixel region of the radiation detector and extends along at least one of two axes orthogonal to each other and defining the incident surface.

7. The radiation imaging apparatus according to claim 1, wherein a structural portion arranged to show a center position in an effective pixel region of the radiation detector is formed inside the first recessed portion.

8. The radiation imaging apparatus according to claim 7, wherein the structural portion is a recessed structural portion having a recessed shape.

9. The radiation imaging apparatus according to claim 7, wherein the structural portion is a protruding structural portion having a protruding shape.

10. The radiation imaging apparatus according to claim 7, wherein the structural portion is a structural portion on which a finger is to be put.

11. The radiation imaging apparatus according to claim 1, wherein the first recessed portion is a recessed portion having a depth equal to or larger than 1 mm.

12. The radiation imaging apparatus according to claim 1, wherein in plan view seen from an incident direction of the radiation, the first recessed portion and the second recessed portion are formed in a region containing positions on a line which passes a gravity center position of the radiation imaging apparatus and extends along at least one of two axes orthogonal to each other and defining the incident surface.

13. The radiation imaging apparatus according to claim 1, wherein a radio wave transmission window is formed in at least one side surface among the plurality of side surfaces.

14. The radiation imaging apparatus according to claim 1, wherein the second recessed portion is not formed in a peripheral region of the back surface adjacent to the second side surface.

* * * * *